(12) United States Patent
Nicholas et al.

(10) Patent No.: US 9,079,159 B2
(45) Date of Patent: Jul. 14, 2015

(54) OLEFIN METATHESIS PROCESS USING A TREATED TUNGSTEN OXIDE CATALYST

(75) Inventors: Christopher P Nicholas, Evanston, IL (US); Mark A. Krawczyk, Chicago, IL (US); Kristoffer E. Popp, Chicago, IL (US); Jennifer F. Abrahamian, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 294 days.

(21) Appl. No.: 13/086,671

(22) Filed: Apr. 14, 2011

(65) Prior Publication Data

US 2012/0264990 A1    Oct. 18, 2012

(51) Int. Cl.
| | |
|---|---|
| C07C 6/04 | (2006.01) |
| C07C 6/02 | (2006.01) |
| B01J 37/18 | (2006.01) |
| B01J 37/08 | (2006.01) |
| B01J 23/30 | (2006.01) |
| B01J 37/02 | (2006.01) |
| B01J 38/04 | (2006.01) |

(52) U.S. Cl.
CPC ....... *B01J 23/30* (2013.01); *B01J 37/18* (2013.01); *C07C 6/04* (2013.01); *B01J 37/0207* (2013.01); *B01J 37/08* (2013.01); *B01J 38/04* (2013.01); *C07C 2521/08* (2013.01); *C07C 2523/30* (2013.01)

(58) Field of Classification Search
USPC .......................................................... 585/646
See application file for complete search history.

(56) References Cited

U.S. PATENT DOCUMENTS

| | | | |
|---|---|---|---|
| 3,274,124 A | | 9/1966 | O'Hara |
| 3,909,450 A | | 9/1975 | O'Hara |
| 3,978,150 A | | 8/1976 | McWilliams, Jr. |
| 4,217,244 A | | 8/1980 | Montgomery |
| 4,288,688 A | | 9/1981 | Kiyama et al. |
| 4,727,198 A | * | 2/1988 | Spencer .......... 568/482 |
| 4,988,659 A | | 1/1991 | Pecoraro |
| 5,026,935 A | | 6/1991 | Leyshon et al. |
| 5,026,936 A | | 6/1991 | Leyshon et al. |
| 5,914,433 A | | 6/1999 | Marker |
| 5,981,818 A | * | 11/1999 | Purvis et al. .......... 585/519 |
| 6,858,133 B2 | | 2/2005 | Dath et al. |
| 6,867,341 B1 | | 3/2005 | Abrevaya et al. |

(Continued)

FOREIGN PATENT DOCUMENTS

| | | |
|---|---|---|
| EP | 0057736 B1 * | 5/1981 |
| EP | 0259526 B1 * | 9/1991 |
| EP | 1329455 A1 * | 7/2003 |

OTHER PUBLICATIONS

Grubbs, Olefin metathesis, 2004, Tetrahedron, vol. 60, pp. 7117-7140.*

(Continued)

*Primary Examiner* — In Suk Bullock
*Assistant Examiner* — Youngsul Jeong

(57) ABSTRACT

A process for olefin metathesis is disclosed. The process involves contacting a feedstock comprising a first olefin and a second olefin having a carbon number at least two greater than that of the first olefin with a catalyst comprising a tungsten component on a refractory oxide support, e.g. silica at metathesis conditions to provide a product olefin having an intermediate carbon number between that of the first and second olefin. The catalyst is characterized in that it is first pretreated with hydrogen followed by treatment with ethylene.

17 Claims, 2 Drawing Sheets

Feed conversion at 400°C of various catalyst pretreatments

(56) References Cited

U.S. PATENT DOCUMENTS

| | | |
|---|---|---|
| 7,087,155 B1 | 8/2006 | Dath et al. |
| 7,268,265 B1 | 9/2007 | Stewart et al. |
| 7,375,257 B2 | 5/2008 | Dath et al. |
| 7,459,596 B1 * | 12/2008 | Abrevaya et al. ............. 585/653 |
| 7,586,018 B2 | 9/2009 | Bozzano et al. |
| 2005/0124839 A1 * | 6/2005 | Gartside et al. ............... 585/643 |

OTHER PUBLICATIONS

U.S. Appl. No. 12/701,508, filed Feb. 5, 2010, Krawczyk et al.

Coperet et al., Direct observation of reaction intermediates for a well defined heterogeneous alkene metathesis catalyst, Proc. Nat. Acad. Sci., 2008, pp. 12123-12127, vol. 105.

* cited by examiner

OLEFIN METATHESIS PROCESS USING A TREATED TUNGSTEN OXIDE CATALYST

FIELD OF THE INVENTION

This invention relates to a process for the metathesis of olefins, for example in the production of propylene from olefin feedstocks comprising ethylene and butylene. The process uses a catalyst comprising tungsten oxide ($WO_3$) dispersed on a support such as silica and is characterized in that before carrying out the metathesis reaction, it is treated with hydrogen followed by ethylene at pretreatment conditions.

DESCRIPTION OF RELATED ART

Propylene demand in the petrochemical industry has grown substantially, largely due to its use as a precursor in the production of polypropylene for packaging materials and other commercial products. Other downstream uses of propylene include the manufacture of acrylonitrile, acrylic acid, acrolein, propylene oxide and glycols, plasticizer oxo alcohols, cumene, isopropyl alcohol, and acetone. Currently, the majority of propylene is produced during the steam cracking or pyrolysis of hydrocarbon feedstocks such as natural gas, petroleum liquids, and carbonaceous materials (e.g., coal, recycled plastics, and organic materials). The major product of steam cracking, however, is generally ethylene and not propylene.

Steam cracking involves a very complex combination of reaction and gas recovery systems. Feedstock is charged to a thermal cracking zone in the presence of steam at effective conditions to produce a pyrolysis reactor effluent gas mixture. The mixture is then stabilized and separated into purified components through a sequence of cryogenic and conventional fractionation steps. Generally, the product ethylene is recovered as a low boiling fraction, such as an overhead stream, from an ethylene/ethane splitter column requiring a large number of theoretical stages due to the similar relative volatilities of the ethylene and ethane being separated. Ethylene and propylene yields from steam cracking and other processes may be improved using known methods for the metathesis or disproportionation of $C_4$ and heavier olefins, in combination with a cracking step in the presence of a zeolitic catalyst, as described, for example, in U.S. Pat. No. 5,026,935 and U.S. Pat. No. 5,026,936. The cracking of olefins in hydrocarbon feedstocks, to produce these lighter olefins from $C_4$ mixtures obtained in refineries and steam cracking units, is described in U.S. Pat. No. 6,858,133; U.S. Pat. No. 7,087,155; and U.S. Pat. No. 7,375,257.

Steam cracking, whether or not combined with conventional metathesis and/or olefin cracking steps, does not yield sufficient propylene to satisfy worldwide demand. Other significant sources of propylene are therefore required. These sources include byproducts of fluid catalytic cracking (FCC) and resid fluid catalytic cracking (RFCC), normally targeting gasoline production. FCC is described, for example, in U.S. Pat. No. 4,288,688 and elsewhere. A mixed, olefinic $C_3/C_4$ byproduct stream of FCC may be purified in propylene to polymer grade specifications by the separation of $C_4$ hydrocarbons, propane, ethane, and other compounds.

Much of the current propylene production is therefore not "on purpose," but as a byproduct of ethylene and gasoline production. This leads to difficulties in coupling propylene production capacity with its demand in the marketplace. Moreover, much of the new steam cracking capacity will be based on using ethane as a feedstock, which typically produces only ethylene as a final product. Although some hydrocarbons heavier than ethylene are present, they are generally not produced in quantities sufficient to allow for their recovery in an economical manner. In view of the current high growth rate of propylene demand, this reduced quantity of co-produced propylene from steam cracking will only serve to accelerate the increase in propylene demand and value in the marketplace.

A dedicated route to light olefins including propylene is paraffin dehydrogenation, as described in U.S. Pat. No. 3,978,150 and elsewhere. However, the significant capital cost of a propane dehydrogenation plant is normally justified only in cases of large-scale propylene production units (e.g., typically 250,000 metric tons per year or more). The substantial supply of propane feedstock required to maintain this capacity is typically available from propane-rich liquefied petroleum gas (LPG) streams from gas plant sources. Other processes for the targeted production of light olefins involve high severity catalytic cracking of naphtha and other hydrocarbon fractions. A catalytic naphtha cracking process of commercial importance is described in U.S. Pat. No. 6,867,341.

More recently, the desire for propylene and other light olefins from alternative, non-petroleum based feeds has led to the use of oxygenates such as alcohols and, more particularly, methanol, ethanol, and higher alcohols or their derivatives. Methanol, in particular, is useful in a methanol-to-olefin (MTO) conversion process described, for example, in U.S. Pat. No. 5,914,433. The yield of light olefins from such processes may be improved using olefin cracking to convert some or all of the $C_4^+$ product of MTO in an olefin cracking reactor, as described in U.S. Pat. No. 7,268,265. An oxygenate to light olefins conversion process in which the yield of propylene is increased through the use of dimerization of ethylene and metathesis of ethylene and butylene, both products of the conversion process, is described in U.S. Pat. No. 7,586,018.

Despite the use of various dedicated and non-dedicated routes for generating light olefins industrially, the demand for propylene continues to outpace the capacity of such conventional processes. Moreover, further demand growth for propylene is expected. A need therefore exists for cost-effective methods that can increase propylene yields from both existing refinery hydrocarbons based on crude oil as well as non-petroleum derived feed sources.

SUMMARY OF THE INVENTION

The invention relates to a process for olefin metathesis, especially a process for the production of propylene. The process comprises contacting a hydrocarbon feedstock, comprising olefins, the olefins comprising a first olefin and a second olefin having a carbon number of at least two greater than that of the first olefin, with a catalyst comprising a tungsten component dispersed on a refectory oxide support at metathesis reaction conditions, to produce a product olefin having a carbon number intermediate between that of the first and second olefin, the catalyst characterized in that it has been pretreated at pretreatment conditions. In a particular embodiment, the first olefin is ethylene, the second olefin is butylene and the product olefin is propylene. The catalyst comprises tungsten oxide on a silica support and has been treated first by contacting with hydrogen at a temperature of about 400° C. to about 600° C. for a time of about 10 min to about 3 hours, followed by contacting with ethylene at a temperature of about 200° C. to about 300° C. for a time of about 1 hour to about 24 hr.

In a further embodiment, the feedstock comprises ethylene and butylene in an ethylene:butylene molar ratio from about 0.5:1 to about 3:1.

These and other objects, embodiments and details of the invention will become apparent after a detailed description of the invention.

DETAILED DESCRIPTION

Figure 1:
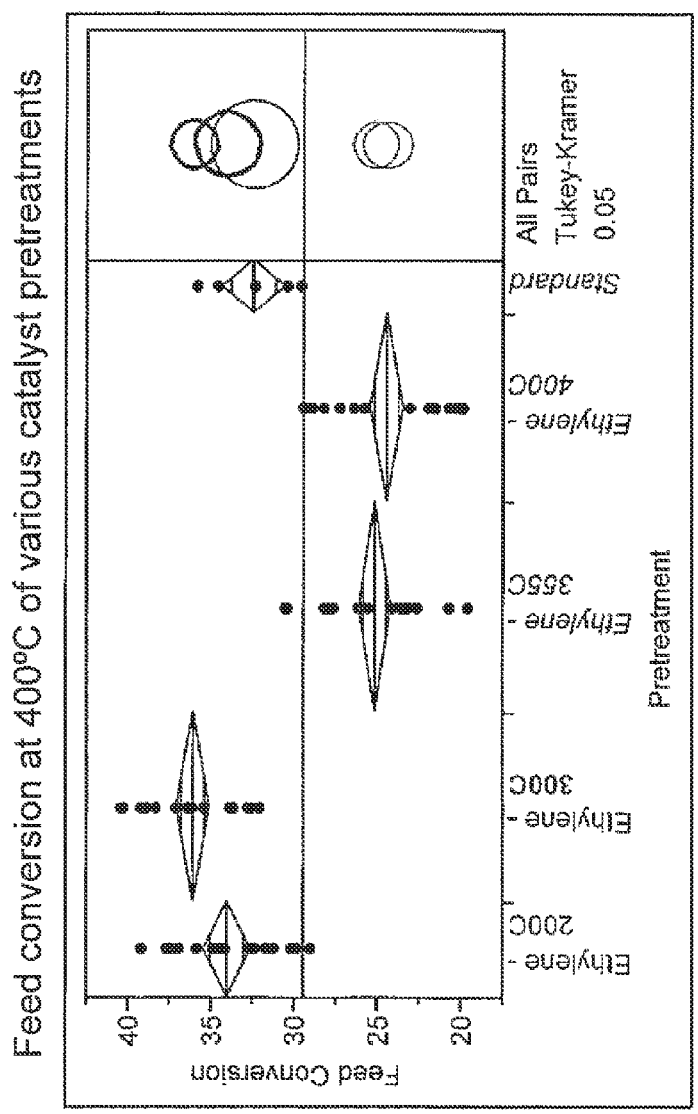
FIG. 1 shows the conversion of feed over a catalyst treated at 5 different pretreatment conditions at a catalyst temperature of 400° C.

As discussed above, the present invention is associated with catalytic olefin metathesis (or disproportionation) processes in which a hydrocarbon feedstock is contacted, in a metathesis reactor or reaction zone, with a catalyst comprising tungsten dispersed on a refractory inorganic oxide support such as silica. The hydrocarbon feedstock refers to the total, combined feed, including any recycle hydrocarbon streams, to the catalyst in the metathesis reactor or reaction zone, but not including any non-hydrocarbon gaseous diluents (e.g., nitrogen), which may be added along with the feed according to some embodiments. The hydrocarbon feedstock may, but does not necessarily, comprise only hydrocarbons. The hydrocarbon feedstock generally comprises predominantly (i.e., at least 50% by weight) hydrocarbons, typically comprises at least about 80% (e.g., from about 80% to about 100%) hydrocarbons, and often comprises at least about 90% (e.g., from about 90% to about 100% by weight) hydrocarbons.

Also, in olefin metathesis processes according to the present invention, the hydrocarbons contained in the hydrocarbon feedstock are generally predominantly (i.e., at least 50% by weight, such as from about 60% to about 100% by weight) olefins, typically they comprise at least about 75% (e.g., from about 75% to about 100%) by weight olefins, and often they comprise at least about 85% (e.g., from about 85% to about 100% or from about 95% to about 100%) by weight olefins. In other embodiments, these amounts of olefins are representative of the total olefin percentages in the hydrocarbon feedstock itself, rather than the olefin percentages of the hydrocarbons in the hydrocarbon feedstock. In yet further embodiments, these amounts of olefins are representative of the total percentage of two particular olefins in the hydrocarbon feedstock, having differing carbon numbers, which can combine in the metathesis reactor or reaction zone to produce a product olefin having an intermediate carbon number (i.e., having a carbon number intermediate to that of (i) a first olefin (or first olefin reactant) and (ii) a second olefin (or second olefin reactant) having a carbon number of at least two greater than that of the first olefin). In general, the two olefins are present in the hydrocarbon feedstock to the metathesis reactor in a molar ratio of the first olefin to the second olefin from about 0.2:1 to about 10:1, typically from about 0.5:1 to about 3:1, and often from about 1:1 to about 2:1.

In an exemplary embodiment, the two olefins (first and second olefins) of interest are ethylene (having two carbons) and butylene (having four carbons), which combine in the metathesis reactor or reaction zone to produce propylene (having three carbons). The term "butylene" is meant to encompass the various isomers of the $C_4$ olefin butene, namely butene-1, cis-butene-2, trans-butene-2, and isobutene. In the case of metathesis reactions involving butylene, it is preferred that the butylene comprises predominantly (i.e., greater than about 50% by weight) butene-2 (both cis and trans isomers) and typically comprises at least about 85% (e.g., from about 85% to about 100%) butene-2, as butene-2 is generally more selectively converted, relative to butene-1 and isobutylene, to the desired product (e.g., propylene) in the metathesis reactor or reaction zone. In some cases, it may be desirable to increase the butene-2 content of butylene, for example to achieve these ranges, by subjecting butylene to isomerization to convert butene-1 and isobutylene, contained in the butylene, to additional butene-2. The isomerization may be performed in a reactor that is separate from the reactor used for olefin metathesis. Alternatively, the isomerization may be performed in an isomerization reaction zone in the same reactor that contains an olefin metathesis reaction zone, for example by incorporating an isomerization catalyst upstream of the olefin metathesis catalyst or even by combining the two catalysts in a single catalyst bed. Suitable catalysts for carrying out the desired isomerization to increase the content of butene-2 in the butylene are known in the art and include, for example, magnesium oxide containing isomerization catalysts as described in U.S. Pat. No. 4,217,244.

As discussed above, the olefins may be derived from petroleum or non-petroleum sources. Crude oil refining operations yielding olefins, and particularly butylene, include hydrocarbon cracking processes carried out in the substantial absence of hydrogen, such as fluid catalytic cracking (FCC) and resid catalytic cracking (RCC). Olefins such as ethylene and butylene are recovered in enriched concentrations from known separations, including fractionation, of the total reactor effluents from these processes. Another significant source of ethylene is steam cracking, as discussed above. A stream enriched in ethylene is generally recovered from an ethylene/ethane splitter as a low boiling fraction, relative to the feed to the splitter, which fractionates at least some of the total effluent from the steam cracker and/or other ethylene containing streams. In the case of olefins derived from non-petroleum sources, both the ethylene and butylene, for example, may be obtained as products of an oxygenate to olefins conversion process, and particularly a methanol to light olefins conversion process. Such processes are known in the art, as discussed above, and optionally include additional conversion steps to increase the butylene yield such as by dimerization of ethylene and/or selective saturation of butadiene, as described in U.S. Pat. No. 7,586,018. According to various embodiments of the invention, therefore, at least a portion of the ethylene in the hydrocarbon feedstock is obtained from a low boiling fraction of an ethylene/ethane splitter and/or at least a portion of the butylene is obtained from an oxygenate to olefins conversion process.

In representative olefin metathesis processes, with an exemplary process being the metathesis of ethylene and butylene for the production of propylene, catalysts comprising tungsten (e.g., as tungsten oxide prior to use in olefin metathesis) supported on silica that is acid washed, may be used to achieve economically favorable product yields under commercial process conditions. With respect to the first and second olefins (e.g., ethylene and butylene) that undergo metathesis, the conversion level, based on the amount of carbon in these reactants that are converted to the desired product and byproducts (e.g., propylene and heavier, $C_5^+$ hydrocarbons), is generally from about 40% to about 80% by weight, and typically from about 50% to about 75% by weight. Significantly higher conversion levels, on a "per pass" basis through the metathesis reactor or reaction zone, are normally difficult to achieve due to equilibrium limitations, with the maximum conversion depending on the specific olefin reactants and their concentrations as well as process conditions (e.g., temperature).

In one or more separations (e.g., fractionation) downstream of the metathesis reactor or reaction zone, the desired product (e.g., propylene) may be recovered in substantially pure form by removing and recovering unconverted olefins (e.g., ethylene and butylene) as well as reaction byproducts (e.g., $C_5^+$ hydrocarbons including olefin oligomers and alkylbenzenes). Recycling of the unconverted olefin reactants back to the metathesis reactor or reaction zone may often be desirable for achieving complete or substantially complete overall conversion, or at least significantly higher overall conversion (e.g., from about 80% to about 100% by weight, or from about 95% to about 100% by weight) than the equilibrium-limited per pass conversion levels discussed above. The downstream separation(s) are normally carried out to achieve a high purity of the desired product, particularly in the case of propylene. For example, the propylene product typically has a purity of at least about 99% by volume, and often at least about 99.5% by volume to meet polymer grade specifications. According to other embodiments, the propylene purity may be lower, depending on the end use of this product. For example, a purity of at least about 95% (e.g., in the range from about 95% to about 99%) by volume may be acceptable for a non-polymer technology such as acrylonitrile production, or otherwise for polypropylene production processes that can accommodate a lower purity propylene.

At the per pass conversion levels discussed above, the selectivity of the converted feedstock olefin components (e.g., ethylene and propylene) to the desired olefin(s) (e.g., propylene) having an intermediate carbon number is generally at least about 75% (e.g., in the range from about 75% to about 100%) by weight, typically at least about 80% (e.g., in the range from about 80% to about 99%) by weight, and often at least about 90% (e.g., in the range from about 90% to about 97%) by weight, based on the amount of carbon in the converted products. The per pass yield of the desired olefin(s) is the product of the selectivity to this/these product(s) and the per pass conversion, which may be within the ranges discussed above. The overall yield, using separation and recycle of the unconverted olefin reactants as discussed above, can approach this/these product selectivity/selectivities, as essentially complete conversion is obtained (minus some purge and solution losses of feedstock and product(s), as well as losses due to downstream separation inefficiencies).

The conversion and selectivity values discussed above are achieved by contacting the hydrocarbon feedstock described above, either continuously or batchwise, with a catalyst as described herein comprising tungsten disposed on a support comprising silica. Optionally, the silica may have been acid washed prior to the tungsten impregnation. Generally, the contacting is performed with the hydrocarbon feedstock being passed continuously through a fixed bed of the catalyst in an olefin metathesis reactor or reaction zone. For example, a swing bed system may be utilized, in which the flowing hydrocarbon feedstock is periodically re-routed to (i) bypass a bed of catalyst that has become spent or deactivated and (ii) subsequently contact a bed of fresh catalyst. A number of other suitable systems for carrying out the hydrocarbon/feedstock contacting are known in the art, with the optimal choice depending on the particular feedstock, rate of catalyst deactivation, and other factors. Such systems include moving bed systems (e.g., counter-current flow systems, radial flow systems, etc.) and fluidized bed systems, any of which may be integrated with continuous catalyst regeneration, as is known in the art.

Representative conditions for olefin metathesis (i.e., conditions for contacting the hydrocarbon feedstock and catalyst in the olefin metathesis reactor or reaction zone), in which the above conversion and selectivity levels may be obtained, include a temperature from about 300° C. (572° F.) to about 600° C. (1112° F.), and often from about 400° C. (752° F.) to about 500° C. (932° F.); a pressure from about 1000 kPag (145 psig) to about 8000 kPag (1160 psig), and often from about 1500 kPag (218 psig) to about 4500 kPag (653 psig); and a liquid hourly space velocity (LHSV) from about 0.1 $hr^{-1}$ to about 10 $hr^{-1}$. As is understood in the art, the LHSV is the volume flow of the hydrocarbon feedstock divided by the volume of the catalyst bed and represents the equivalent catalyst bed volumes of feed processed every hour. The LHSV is related to the inverse of the reactor residence time. Under the olefin metathesis conditions described above, the hydrocarbon feedstock is normally in the vapor phase in the olefin metathesis reactor or reaction zone, but it may also be in the liquid phase, for example, in the case of heavier (higher carbon number) olefin feedstocks.

As stated, the metathesis catalyst comprises a tungsten component dispersed on a refractory oxide support. The refractory oxide support is selected from the group consisting of silica, aluminas, silica-alumina, zirconia, titania, boria, thoria, ceria and mixtures thereof. In order to avoid confusion it is pointed out that the term silica-alumina does not mean a physical mixture of silica and alumina but means an acidic and amorphous material that has been cogelled or coprecipitated. The term is well known in the art; see e.g. U.S. Pat. No. 3,909,450; U.S. Pat. No. 3,274,124 and U.S. Pat. No. 4,988,659. A preferred support is a silica support and an especially preferred support is an acid washed silica support (See, U.S. application Ser. No. 12/701,508).

The types of silica which can be used as the support include amorphous silica and crystalline silica. Examples of amorphous silica which are commercially available include Davisil® 646, Davisil® 636 (W.R. Grace & Co., Columbia, Md.) and other precipitated silicas. Particularly advantageous results are obtained with silica, after acid washing. Generally the silica (whether acid washed or not) has a surface area of at least about 250 square meters per gram ($m^2/g$), with exemplary surface areas being in the range from about 250 $m^2/g$ to about 600 $m^2/g$, and often from about 300 $m^2/g$ to about 500 $m^2/g$. The average pore diameter (or pore size) of the amorphous silica, after acid washing, is at least about 40 angstroms (Å), with exemplary average pore diameters being in the range from about 45 Å to about 170 Å, and preferably in the range from about 45 Å to about 100 Å. Surface area and average pore diameter are measured according to the Brunauer, Emmett and Teller (BET) method based on nitrogen adsorption (ASTM D1993-03 (2008)).

Crystalline silicas may also be used as the silica support. Crystalline silica as used herein refers to those microporous or mesoporous crystalline materials which are substantially all silica. One such example is the mesoporous materials MCM-41. Crystalline silicas have a silica to alumina molar ratio of at least about 1,000 corresponding to an atomic silicon to aluminum ratio (Si:Al ratio) of at least about 500. Typically, the crystalline silica will have a silica to alumina molar ratio of at least about 3,000 (e.g., from about 3,000 to about 15,000), and often at least about 5,000 (e.g., from about 5,000 to about 10,000).

The refractory oxide support, e.g. silica support and consequently the catalyst itself can have a number of possible physical forms, with the specific form usually depending principally on the particular reaction system used. The support may be, for example, in the form of a powder that is sized to a desired average particle size, for example from about 35 mesh (0.50 mm) to about 60 mesh (0.25 mm). In reaction systems where a powder form would lead to an undesirably high pressure drop, larger spheres or extrudates (e.g., in the form of elongated cylinders) are commonly employed, with the specific shape being determined by factors such as pressure drop, mobility, diffusional distance, etc. In representative embodiments, the support has an average particle size, based on a representative dimension of the particle form (e.g., the diameter of a spherical form or the diameter of the circular cross section of a cylindrical, extruded form) from about 0.1 mm to about 5 mm.

As stated, it is preferred to acid wash the silica support. Acid washing of the silica support involves contacting the silica with an acid, which can be an organic acid or an inorganic acid. Particular inorganic acids include nitric acid, sulfuric acid, and hydrochloric acid, with nitric acid and hydrochloric acid being preferred. The acid used for the acid washing usually has a concentration from about 0.05 molar (M) to about 3 M, and often from about 0.1 M to about 1 M. The acid washing can be performed under static conditions (e.g., batch) or flowing conditions (e.g., once-through, recycle, or with a combined flow of make-up and recycle solution).

Representative contacting conditions for acid washing the silica include a temperature from about 20° C. (68° F.) to about 120° C. (248° F.), typically from about 30° C. (86° F.) to about 100° C. (212° F.), and often from about 50° C. (122° F.) to about 90° C. (194° F.). The time during which the silica is contacted with the acid is generally from about 10 minutes to about 5 hours, and often from about 30 minutes to about 3 hours. Finally, the acid washed silica is dried. Drying conditions include a temperature from about 25° C. (77° F.) to about 250° C. (482° F.) and a time from about 0.5 hours to about 24 hours.

Again using silica as an exemplary support and regardless of whether the silica is acid washed or not, the support is impregnated with a tungsten compound to provide a tungsten impregnated silica support. Impregnation generally involves contacting the silica support with an impregnation solution of the tungsten compound. Suitable compounds include, but are not limited to, ammonium tungstate compounds such as ammonium metatungstate (AMT) and ammonium paratungstate (APT). The concentration of the tungsten compound in such impregnation solutions generally ranges from about 0.1 M to about 5 M. As discussed above with respect to acid washing, static or flowing conditions may be used for contacting the impregnation solution with the silica support to impregnate the desired amount of tungsten compound. The impregnation conditions include a temperature from about 20° C. (68° F.) to about 200° C. (392° F.), and often from about 25° C. (77° F.) to about 150° C. (302° F.) and a contact time from about 1 minute to about 5 hours and often from about 5 minutes to about 3 hours. The impregnation conditions are selected to achieve a desired level of tungsten (as tungsten metal), from about 1% to about 10% by weight, in the resulting catalyst.

Following impregnation, the tungsten impregnated support is dried and then calcined to convert the tungsten compound to tungsten oxide ($WO_3$). Drying conditions include a temperature from about 25° C. (77° F.) to about 250° C. (482° F.) and a time from about 0.5 hours to about 24 hours. Calcining conditions that are effective for converting all or substantially all of the tungsten compound to $WO_3$ involve heating the tungsten impregnated support (either immediately after impregnation or after drying) to a temperature from about 300° C. (572° F.) to about 750° C. (1382° F.), and often from about 400° C. (752° F.) to about 650° C. (1202° F.), for a time from about 1 hour to about 10 hours, and often from about 3 hours to about 9 hours. Both the drying and calcining steps are normally performed with a flow of oxygen-containing gas (e.g., air, oxygen, or oxygen-enriched air). It should be pointed out that the drying step can be combined with the calcining step, i.e. drying occurs during calcination.

After calcination, the tungsten oxide is reduced in the presence of flowing hydrogen, the conversion may occur, for example, shortly prior to use or in situ. Regardless of whether the reduction is carried out separately or in situ, the reduction conditions comprise flowing hydrogen at a temperature of about 400° C. (752° F.) to about 600° C. (1112° F.) for a time of about 10 minutes to about 4 hours.

Following the hydrogen reduction, the catalyst is then exposed to flowing ethylene at a temperature from about 200° C. (392° F.) to about 350° C. (662° F.) for a time of about 1 hour to about 24 hours prior to starting the olefin metathesis feed. Without being bound by theory, it is thought that these benefits result from the efficient generation of silica-supported tungsten carbenes from the supported tungsten oxide precursors. Tungsten carbenes have been shown to be the putative active species in olefin metathesis catalysts (Coperet, et. al. *Proc. Nat. Acad. Sci.* 2008, 105, 12123-7.), so improved efficiency in their generation would lead to higher conversion levels. Increased olefin metathesis activity may be exploited commercially by reducing the requirement to heat the olefin-containing hydrocarbon feedstock, prior to its contact with the catalyst at the inlet of the olefin metathesis reaction zone. Alternatively, increased product yield (the product of conversion and selectivity) may be obtained at a given reactor temperature. It will be recognized that cost advantages, associated with decreased energy requirements and/or greater product value, result in either case. In view of the current demand for propylene, it will be appreciated that even a slight improvement in product yield, on the order of only a few percent, can result in substantial economic advantages, on the order of several million dollars per year in increased product value, for a typical petrochemical producer. The improved value of the product slate is accompanied by a reduction in downstream separation requirements for removing non-selective reaction products (e.g., $C_5^+$ olefins), and also a reduction in equipment and utilities required for the recycle of unconverted olefin reactants.

The following examples are representative of the present invention and its associated advantages and are not to be construed as limiting the scope of the invention as set forth in the appended claims.

Example 1

Tungsten Impregnation of Silica Supports and Calcination

Davisil 646 (150 g), a silica sized to 35-60 US mesh (0.25-0.5 mm), was impregnated with tungsten at a targeted tungsten metal content of 6% based on the total dry catalyst weight. A solution of tungstosilicic acid was made by dissolving 11.68 g of $H_4[W_{12}SiO_{40}]$ in 350 g deionized water. The tungsten solution was added to the dry silica in thirds. The wetted, tungsten impregnated silica was then dried at 110° C. for 2 hr then calcined in a muffle oven under air flow ramping at 1° C./min to 250° C., holding at 250° C. for 2 h, then ramping at 3° C./min to 550° C. (932° F.) and holding there for 8 h. The resulting tungsten oxide on silica catalyst was then evaluated, after a variety of pretreatment conditions, for its performance in the metathesis of ethylene and butylene to produce propylene, as described below in Example 2.

Example 2

Evaluation of Tungsten Oxide Catalysts, with Various Pretreatments

The catalyst prepared in Example 1 was evaluated for metathesis of an ethylene and butylene feedstock to produce propylene in a high-throughput experimental protocol. Samples of the catalysts, 200 microliter (μl) each, were tested in a microreactor array system (High Pressure Reactor Assay Module from Sintef (Trondheim, Norway)) equipped with a gas and liquid flow control module, reactor/oven assembly, and analytical section providing 48 individual reactor channels. The catalysts were reduced for 45 minutes at 500° C. (932° F.) under flowing hydrogen. Following the $H_2$ reduction, the temperature was reduced and the feed switched. The standard pretreatment was to switch to the ethylene/butene feed described below and after 5 hours of lineout at 343° C., to acquire the first data point. For ethylene pretreatments, the temperature was reduced to 200° C., 300° C., 355° C. or 400° C. After 10 hours at one of these pretreatment conditions, the temperature was changed to 343° C. and after 5 hours of lineout, the first data point was acquired. The tests were performed at catalyst bed temperatures of 343° C. (649° F.), 400° C. (752° F.), 425° C. (797° F.), and 343° C. (649° F.), respectively. The four temperature conditions were evaluated consecutively over durations of 4, 4, 6, and 4 hours, respectively.

A hydrocarbon feedstock of ethylene and butylene at an ethylene:butylene target molar ratio of 1.5 was supplied from cylinders, with the ethylene meeting ultra high purity (UHP) specifications and the butylene being technical grade material containing about 93-95 mole-% cis and trans 2-butenes. The liquid hourly space velocity (LHSV), or volumetric flow rate of the hydrocarbon feedstock divided by the catalyst bed volume, was controlled at 0.9 $hr^{-1}$. Also, the reactor pressure set point was maintained at a target value of 3200 kPag (465 psig) throughout the olefin metathesis testing.

The reactor effluent composition was analyzed periodically using a high-speed gas chromatography method developed to accommodate the high-throughput experimentation. The analytical results were used to determine both the conversion level (per pass), based on the total percentage conversion of feed carbon, and the selectivity, based on the total percentage of converted carbon that resulted in the formation of propylene.

Figure 2:
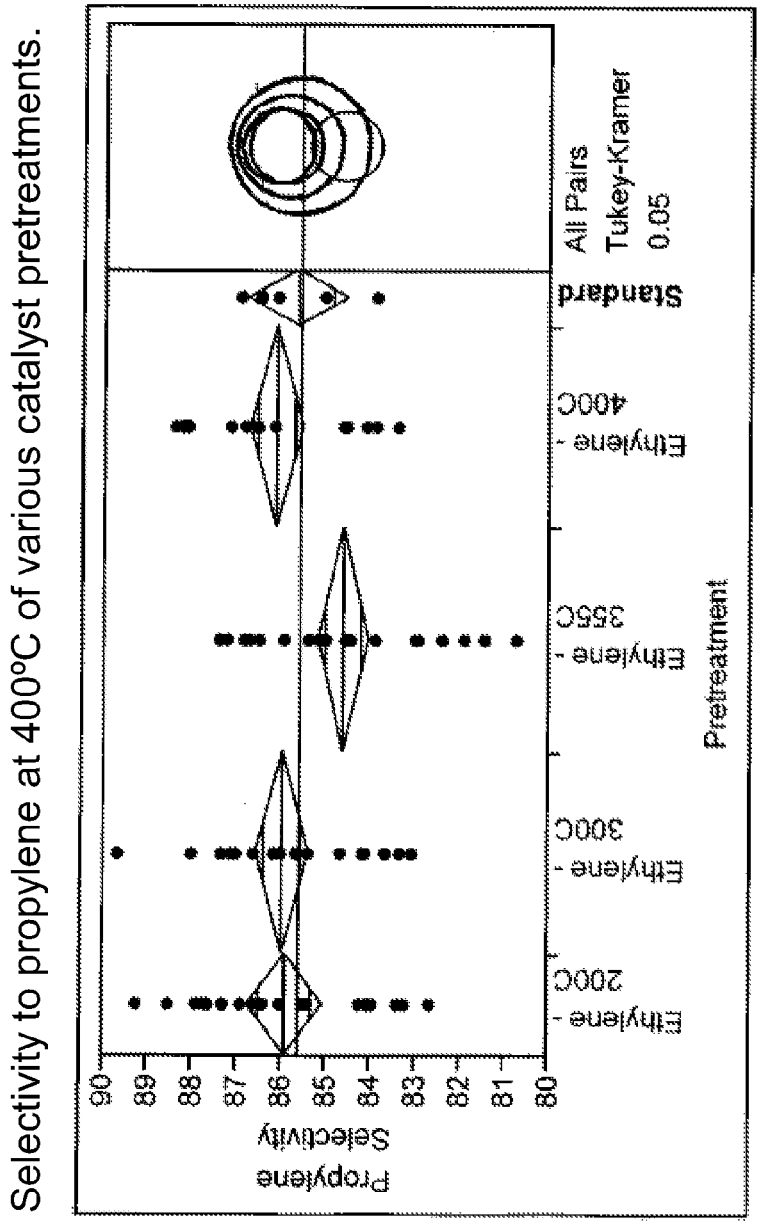
FIG. 2 shows the selectivity to product propylene at this temperature.

For the 5 $WO_3$ on silica support catalysts generated via the various pretreatments prepared in Examples 2, the average propylene selectivity and feed conversion values (per pass) were calculated over the duration of each temperature condition used for olefin metathesis performance evaluation. FIG. 1 shows the conversion of feed at a catalyst temperature of 400° C. FIG. 2 shows the selectivity to product olefin propylene at this temperature. The results in the Figures illustrate that the ethylene pretreated catalysts were more active, meaning that conversion was greater at a given reactor temperature, compared to the reference pretreatment. Moreover, this increase in activity was not obtained at the expense of any loss in selectivity.

In order to determine whether the results presented in FIGS. 1 and 2 are statistically different, the mean for each experiment was analyzed using the Tukey-Kramer HSD test. The Tukey-Kramer HSD is a multiple comparison test and is one of several tests that can be used to determine which means amongst a set of means differ from the rest. The test compares the difference between each pair of means with appropriate adjustment for the variance within each category. A comparison circles plot provides a visual representation of group mean comparisons. Circles for means that are significantly different either do not intersect, or intersect slightly, so that the outside angle of intersection is less than 90 degrees. If the circles intersect by an angle of more than 90 degrees, or if they are nested, the means are not significantly different.

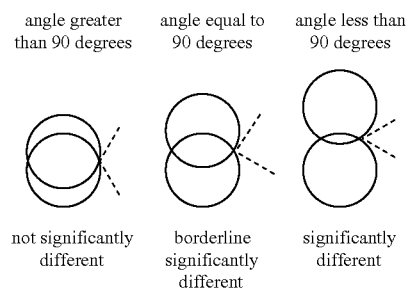

The data presented in FIGS. 1 and 2 were analyzed using the Tukey-Kramer test and the results are presented in Tables 1 and 2 respectively.

TABLE 1

Tukey-Kramer Analysis for FIG. 1

| Pretreatment | Mean (Feed Conversion) | Group 1 | Group 2 | Group 3 |
| --- | --- | --- | --- | --- |
| Ethylene - 300 C. | 36.15 | A | | |
| Ethylene - 200 C. | 34.11 | A | B | |
| Standard | 32.54 | | B | |
| Ethylene - 355 C. | 25.22 | | | C |
| Ethylene - 400 C. | 24.51 | | | C |

TABLE 2

Tukey-Kramer Analysis for FIG. 2

| Pretreatment | Mean (Propylene Selectivity) | Group 1 | Group 2 |
| --- | --- | --- | --- |
| Ethylene - 400 C. | 86.2 | A | |
| Ethylene - 300 C. | 86.0 | A | |
| Ethylene - 200 C. | 85.9 | A | B |
| Standard | 85.7 | A | B |
| Ethylene - 355 C. | 84.6 | | B |

The Tukey-Kramer analysis shows that using a catalyst that has been pretreated with ethylene (at 200 and 300° C.) has statistically better conversion and comparable selectivity to a standard (no ethylene pretreatment) catalyst.

The invention claimed is:
1. An olefin metathesis process comprising:
contacting a hydrocarbon feedstock, comprising olefins, the olefins comprising a first olefin and a second olefin having a carbon number of at least two greater than that of the first olefin, with a catalyst comprising a tungsten component dispersed on a refractory oxide support at metathesis reaction conditions, to produce a product olefin having a carbon number intermediate between that of the first and second olefin, the catalyst characterized in that it has been pretreated at pretreatment condi- tions, where the pretreatment conditions comprise first contacting the catalyst with a hydrogen stream at a temperature from about 400° C. to about 600° C. for a time from about 10 minutes to about 3 hours to produce a hydrogen treated catalyst; followed by contacting the hydrogen treated catalyst with an ethylene stream at a temperature of about 200° C. to about 300° C. for a time of about 1, wherein the first olefin is ethylene, the second olefin is butylene, and the product olefin is propylene.

2. The process of claim 1, wherein the hydrocarbon feedstock comprises at least about 85% by weight olefins.

3. The process of claim 1, wherein the first olefin and the second olefin are present in the hydrocarbon feedstock is at a molar ratio about 0.5:1 to about 3:1.

4. The process of claim 1, wherein at least a portion of the ethylene is obtained from a low boiling fraction of an ethylene/ethane splitter.

5. The process of claim 1, wherein the refractory oxide support comprises silica.

6. The process of claim 5, wherein the silica is an acid washed silica.

7. The process of claim 1, wherein at least a portion of the butylene is obtained from an oxygenate to olefins conversion process or a fluid catalytic cracking process.

8. The process of claim 1, wherein the first olefin and the second olefin are converted to the product olefin with a selectivity of at least about 80% by weight based on the amount of carbon in the converted products.

9. The process of claim 1, wherein the metathesis reaction conditions comprise a temperature from about 300° C. (572° F.) to about 600° C. (1112° F.), a pressure from about 1000 kPag (145 psig) to about 8000 kPag (1160 psig), and a liquid hourly space velocity from about 0.1 $hr^{-1}$ to about 10 $hr^{-1}$.

10. The process of claim 9, wherein the refractory oxide support comprises a crystalline silica and the crystalline silica has a $SiO_2/Al_2O_3$ molar ratio of at least 1000.

11. The process of claim 5, wherein the silica has a BET surface area from about 250 $m^2/g$ to about 600 $m^2/g$, wherein the BET surface area is measured based on nitrogen adsorption.

12. The process of claim 1, wherein the tungsten component is present in an amount from about 1% to about 10% by weight as metal.

13. An olefin metathesis process comprising:

contacting a hydrocarbon feedstock, comprising olefins, the olefins comprising a first olefin and a second olefin having a carbon number of at least two greater than that of the first olefin, with a catalyst comprising a tungsten component dispersed on an acid washed silica support at metathesis reaction conditions, to produce a product olefin having a carbon number intermediate between that of the first and second olefin, the catalyst characterized in that it has been pretreated at pretreatment conditions, where the pretreatment conditions comprise first contacting the catalyst with a hydrogen stream at a temperature from about 400° C. to about 600° C. for a time from about 10 minutes to about 3 hours to produce a hydrogen treated catalyst; followed by contacting the hydrogen treated catalyst with an ethylene stream at a temperature of about 200° C. to about 300° C. for a time of about 1, wherein the first olefin is ethylene, the second olefin is butylene, and the product olefin is propylene.

14. The process of claim 13, wherein the average pore diameter of the silica support, after acid washing, is in the range from about 45 Å to about 170 Å.

15. The process of claim 13, wherein the average pore diameter of the silica support, after acid washing, is in the range from about 45 Å to about 100 Å.

16. The process of claim 13, wherein the tungsten component is present in an amount from about 1% to about 10% by weight as metal.

17. The process of claim 13, wherein the silica support has a BET surface area from about 250 $m^2/g$ to about 600 $m^2/g$, wherein the BET surface area is measured based on nitrogen adsorption.

* * * * *